| (12) | United States Patent<br>Kang | (10) Patent No.: US 12,318,506 B2<br>(45) Date of Patent: *Jun. 3, 2025 |
|---|---|---|

(54) METHOD FOR MANUFACTURING RING-SHAPED BONE GRAFTING SUBSTITUTE

(71) Applicant: PURGO BIOLOGICS INC., Seongnam-si (KR)

(72) Inventor: Ho Chang Kang, Seongnam-si (KR)

(73) Assignee: PURGO BIOLOGICS INC. (KR)

( * ) Notice: Subject to any disclaimer, the term of this patent is extended or adjusted under 35 U.S.C. 154(b) by 1014 days.

This patent is subject to a terminal disclaimer.

(21) Appl. No.: 17/059,206

(22) PCT Filed: Mar. 28, 2019

(86) PCT No.: PCT/KR2019/003637
§ 371 (c)(1),
(2) Date: Nov. 25, 2020

(87) PCT Pub. No.: WO2019/231094
PCT Pub. Date: Dec. 5, 2019

(65) Prior Publication Data
US 2021/0213164 A1    Jul. 15, 2021

(30) Foreign Application Priority Data

May 30, 2018    (KR) .......................... 10-2018-0062008

(51) Int. Cl.
*A61L 27/36*    (2006.01)
*A61L 27/24*    (2006.01)

(52) U.S. Cl.
CPC ............. *A61L 27/365* (2013.01); *A61L 27/24* (2013.01); *A61L 27/3608* (2013.01); *A61L 27/3687* (2013.01); *A61L 2430/02* (2013.01); *A61L 2430/12* (2013.01)

(58) Field of Classification Search
None
See application file for complete search history.

(56) References Cited

U.S. PATENT DOCUMENTS

| 2002/0076429 A1* | 6/2002 | Wironen ................. A61L 27/48 |
|---|---|---|
| | | 424/426 |
| 2002/0091447 A1 | 7/2002 | Shimp et al. |
| 2003/0039676 A1 | 2/2003 | Boyce et al. |
| 2003/0093154 A1 | 5/2003 | Estes et al. |
| 2017/0151040 A1 | 6/2017 | Wychowanski et al. |

FOREIGN PATENT DOCUMENTS

| GB | 2365423 A | 2/2002 |
|---|---|---|
| JP | 2002532159 A | 10/2002 |
| JP | 6157351 B2 | 7/2017 |
| KR | 20150134193 A | 12/2015 |
| KR | 101661725 B1 | 10/2016 |

OTHER PUBLICATIONS

European Extended Search Report for Application No. 19811409.2, mailed Jul. 22, 2021.
International Search Report for PCT/KR2019/003637 mailed Jul. 16, 2019.

* cited by examiner

*Primary Examiner* — David J Blanchard
*Assistant Examiner* — Daniel F Coughlin
(74) *Attorney, Agent, or Firm* — Renaissance IP Law Group LLP

(57) ABSTRACT

Provided is a method for manufacturing a ring-shaped bone grafting substitute. The method for manufacturing a ring-shaped bone grafting substitute includes a biodegradable polymer providing step of providing a biodegradable polymer, a molding material providing step of providing a molding material in which the biodegradable polymer and a bone material are mixed; a molding material injection step of injecting the molding material into a ring-shaped mold such that a hole is formed in the center thereof; and ring-shaped bone grafting substitute molding step of freeze-drying the molding material having been injected into the ring-shaped mold at a temperature lower than a predetermined reference temperature, thereby molding the resultant into a ring-shaped bone grafting substitute.

15 Claims, 7 Drawing Sheets

METHOD FOR MANUFACTURING RING-SHAPED BONE GRAFTING SUBSTITUTE

TECHNICAL FIELD

The present inventive concept relates to a method for manufacturing a ring-shaped bone grafting substitute, and more particularly, to a method for manufacturing a ring-shaped bone grafting substitute which may remarkably reduce an implant treatment period and have a strength enough to firmly fix an implant screw.

BACKGROUND ART

Bone grafting substitute (BGS) is a graft substitute that is used to fill a space in a bone tissue and promotes the formation of a new bone by replacing a lost portion generated in the bone tissue due to various dental diseases or traumas, degeneration due to disease, or other tissue losses.

In detail, when the quality of a bone is poor or the amount of a bone is insufficient during an implant treatment, or when an alveolar bone is destroyed or lost due to periodontitis, an implant may not be placed immediately, so a treatment to increase the alveolar bone is necessary. As such, when osteogenesis (bone composition) is necessary, guided bone regeneration (GBR) or bone grafting may be performed.

BGS may include a bone-derived BGS and a synthetic BGS. The bone-derived BGS may include an autogenous bone, an allogenic bone, and a xenogenic bone. The autogenous bone has demerits of inconveniently performing a surgery and being absorbed too quickly. In contrast, the allogenic bone graft has possibilities of an immune response and a viral and disease infection. For the case of a synthetic bone that is artificially manufactured, while there is no possibility of infection of virus and disease, bone regenerability is lowered and absorption is too fast, compared with the bone-derived bone. To address the above demerits, the xenogenic BGS derived from an animal's bone having a structure similar to human's bone is being used.

When alveolar bone regeneration is completed through the above-described GBR, an implant is placed through a secondary surgery in which a gum is cut and an implant screw is inserted. As the regeneration of the alveolar bone requires about 6 months for completion, and implant placement is performed the secondary surgery, long time is needed from the alveolar bone regeneration to the implant placement.

To solve the above problems, there is a demand for a method that may remarkably shorten a time for performing an implant treatment by inserting an implant into a screw that has first inserted without the secondary treatment, unlike a conventional method of performing a secondary surgery by removing a tooth from a periodontal tissue of an oral cavity, placing a BGS in a cavity of the periodontal tissue from which the tooth is removed, inserting an implant screw therein and then suturing the cavity by covering the implant screw with a membrane thereon, and when alveolar bone regeneration is completed, cutting a gum and inserting an implant screw therein.

DETAILED DESCRIPTION OF THE INVENTIVE CONCEPT

Technical Problem

The present inventive concept provides a method for manufacturing a ring-shaped bone grafting substitute, in which a bone grafting substitute has a ring shape so that an implant treatment period may be remarkably shortened by simultaneously performing the implantation of a bone grafting substitute and the placement of an implant, and the bone grafting substitute may have a strength enough to firmly fix an implant screw.

Solution to Problem

According to an aspect of the present inventive concept, a method for manufacturing a ring-shaped bone grafting substitute includes a biodegradable polymer providing step of providing a biodegradable polymer, a molding material providing step of providing a molding material by mixing the biodegradable polymer with a bone material, a molding material injection step of injecting the molding material into a ring-shaped mold having a ring shape to form a hole at a center, and a ring-shaped bone grafting substitute molding step of molding a ring-shaped bone grafting substitute having a ring shape by freeze-drying the molding material injected into the ring-shaped mold at a temperature lower than a predetermined reference temperature.

The method may further include, after the ring-shaped bone grafting substitute molding step, a ring-shaped bone grafting substitute hot air drying step of drying, by using hot air, the ring-shaped bone grafting substitute that has been completely molded.

The method may further include, before the ring-shaped bone grafting substitute hot air drying step a ring-shaped bone grafting substitute cutting step of cutting the ring-shaped bone grafting substitute in a unit size, and a dehydration step of removing moisture included in the ring-shaped bone grafting substitute.

The biodegradable polymer may include collagen, the collagen includes collagen from porcine ligament, and the collagen providing step of providing the collagen may include a pig ligament preprocessing step of preprocessing the pig ligament to obtain collagen from the pig ligament, a collagen dough molding step of molding a preprocessed pig ligament into a collagen dough, a homogenization step of dissolving the collagen dough in a solvent to produce a homogenized collagen solution, and a collagen filtering step of filtering collagen from the homogenized collagen solution.

The pig ligament preprocessing step may include a step of removing at least blood vessels and fat from the pig ligament, a step of dissolving the pig ligament where at least blood vessels and fat are removed in a 10% iso-propyl alcohol (IPA) aqueous solution, a step of providing a cured pig ligament by curing a solution where the pig ligament is dissolved at a temperature lower than a predetermined reference temperature, and a step of cutting the cured pig ligament in a predetermined size.

The collagen dough molding step may include a step of adding the preprocessed pig ligament to a 3% acetic acid aqueous solution where pepsin is dissolved, and mixing the resultant by using a Stephan mixer, a step of providing a first mixture by adding a 3% acetic acid aqueous solution to a mixed solution and agitating the resultant for 5-7 minutes, a step of providing a first dough by removing, by using a press machine, liquid from the first mixture obtained by the agitation, a step of providing a second mixture by adding the first dough to an aqueous solution obtained by dissolving $Na_2HPO_4$ in purified water and agitating the resultant, a step of providing a second dough by removing, by using a press machine, liquid from the second mixture obtained by the agitation, a step of providing a third mixture by adding the second dough to a 15% iso-propyl alcohol (IPA) aqueous solution and agitating the resultant by using a Stephan mixer, and a step of molding a collagen dough by removing, by using a press machine, liquid from the third mixture obtained by the agitation.

The collagen filtering step may include a step of centrifuging the homogenized collagen solution, and a step of obtaining collagen by removing supernatant liquid generated after the centrifugation.

The biodegradable polymer may include collagen, the collagen includes collagen from porcine skin, and a collagen providing step of providing the collagen includes a porcine skin preprocessing step of preprocessing the porcine skin to obtain collagen from the porcine skin, a homogenization step of dissolving the preprocessed porcine skin in a solvent to produce a homogenized collagen solution, and a collagen filtering step of filtering collagen from the homogenized collagen solution.

The porcine skin preprocessing step may include a step of cutting frozen porcine skin in a predetermined size, a step of removing fat by adding cut porcine skin to acetone and agitating the resultant, and a step of removing acetone by washing porcine skin where fat is removed, with distilled water.

The collagen filtering step may include a step of centrifuging the homogenized collagen solution, a step of dissolving a precipitate generated from the centrifugation in a HCL aqueous solution, and a step of obtaining collagen by decompression filtering a supernatant liquid generated by centrifuging a solution obtained by dissolving the precipitate in the HCL aqueous solution.

The collagen may include crosslinked collagen that is crosslinked to have a crosslink structure, and the method may further include, after the collagen filtering step a fibrillation buffer mixing step of providing a mixed solution obtained by mixing the collagen obtained from the collagen filtering step with a fibrillation buffer having sodium chloride 20-30 part by weight, sodium hydroxide 1-3 part by weight, and di-sodium hydrogen phosphate dihydrate 3-5 part by weight with respect to water 100 part by weight, a gel state change step of providing a mixture in a gel state by mixing the mixed solution with gamma polyglutamic acid (γ-PGA) and putting the resultant in a well plate to be changed to a gel state in an incubator, a crosslink reaction processing step of forming crosslinked collagen by mixing the gel state mixture with a crosslinking solution to induce a crosslink reaction, a washing step of washing the crosslinking solution mixed in the crosslink reaction processing step, an after-crosslink-processing homogenization step of dissolving the crosslinked collagen in a solvent to produce a homogenized crosslinked collagen solution, and a crosslinked collagen filtering step of filtering crosslinked collagen from the homogenized crosslinked collagen solution.

The washing step may include a step of providing a first mixture by tearing the crosslinked collagen into small pieces and adding the resultant to a 15% ethanol aqueous solution, a step of providing a filtrate by agitating the first mixture and decompression filtering the resultant, a step of providing a second mixture by tearing the filtrate into small pieces and adding the resultant to a 15% ethanol aqueous solution, and a step of agitating the second mixture and decompression filtering the resultant.

The biodegradable polymer may comprise any one selected from among fibrinogen, chitosan, gelatin, cellulose, hyaluronic acid, dextran, crosslinked collagen, crosslinked fibrinogen, crosslinked chitosan, crosslinked gelatin, crosslinked cellulose, crosslinked hyaluronic acid, crosslinked dextran, which are crosslinked to have a crosslink structure, polycaprolactone, polylactic acid, polyglycolic acid, and a copolymer of lactic acid and glycolic acid.

The bone material may include any one xenogenic bone selected from among a cattle bone, a horse bone, and a pig bone.

The bone material may include a synthetic bone that is artificially synthetized.

In the molding material providing step, the bone material and the biodegradable polymer may be mixed such that a weight ratio of bone material/biodegradable polymer is 60/40 to 95/5.

The biodegradable polymer may include collagen, and the bone material and the collagen may be mixed such that a weight ratio of bone material/collagen is 80/20 to 95/5.

In the ring-shaped bone grafting substitute, the ring shape may have a thickness of 2 mm-4 mm.

In the ring-shaped bone grafting substitute, the hole at the center may have a diameter of 3 mm-8 mm and a height of 4 mm-10 mm.

Advantageous Effects

According to the embodiments of the present inventive concept, as a ring-shaped bone grafting substitute is molded, the implantation of a bone grafting substitute and the placement of an implant may be simultaneously performed. Accordingly, an implant treatment period without a secondary surgical operation may be remarkably shortened.

Furthermore, as a ring-shaped bone grafting substitute is molded by mixing collagen and a bone material, a ring-shaped bone grafting substitute having a strength enough to firmly fix an implant screw may be manufactured.

MODE OF THE INVENTIVE CONCEPT

Figure 1:
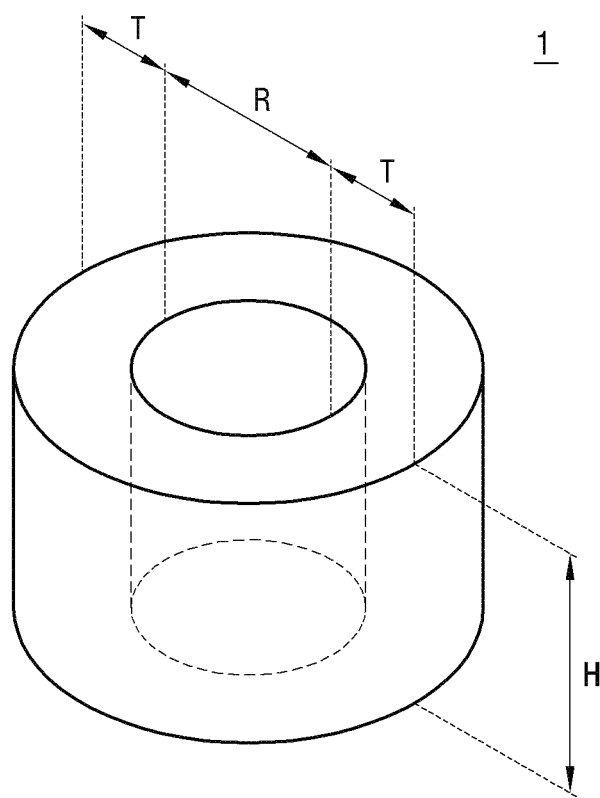
FIG. 1 is a perspective view of a ring-shaped bone grafting substitute according to an embodiment of the present inventive concept.

In order to fully understand the operational advantages of the present inventive concept and the objectives achieved by the implementation of the present inventive concept, the accompanying drawings illustrating preferred embodiments of the present inventive concept and the contents described in the accompanying drawings are referred to.

Hereinafter, the inventive concept will be described in detail by explaining preferred embodiments of the inventive concept with reference to the attached drawings. Like reference numerals in the drawings denote like elements.

FIG. 1 is a perspective view of a ring-shaped bone grafting substitute according to an embodiment of the present inventive concept.

Figure 2:
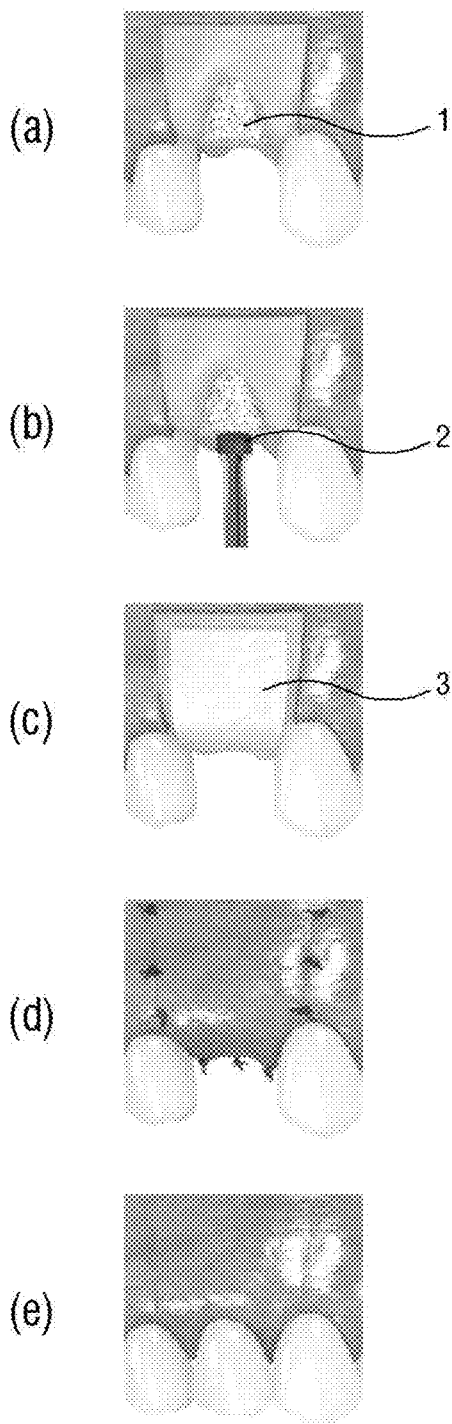
FIG. 2 is a bone implantation surgery process using a ring-shaped bone grafting substitute according to an embodiment of the present inventive concept.

FIG. 2 is a bone implantation surgery process using a ring-shaped bone grafting substitute according to an embodiment of the present inventive concept.

As illustrated in the drawings, a ring-shaped bone grafting substitute 1 according to an embodiment of the present inventive concept has a hole having a diameter R at a center thereof, and has a ring shape in which the thickness of a ring shape is T and the height is H.

As the ring-shaped bone grafting substitute 1 is molded to have a ring shape, unlike the conventional method of performing a secondary surgical operation of placing the ring-shaped bone grafting substitute 1 in a periodontal tissue extraction socket (a cavity of a periodontal tissue from which a tooth is extracted) in an oral cavity, inserting an implant screw into the center hole of the ring-shaped bone grafting substitute 1, covering the socket with a membrane and suturing the cavity, and when alveolar bone regeneration is completed, cutting a gum to insert an implant screw, a time for an implant treatment may be remarkably shortened by inserting an implant into the implant screw that has already been inserted, without the secondary surgical operation.

In this regard, referring to FIG. 2, in step (a), after a tooth is extracted, the ring-shaped bone grafting substitute 1 manufactured according to an embodiment of the present inventive concept is inserted into a hole where an alveolar bone is destroyed; in step (b), an implant screw 2 is inserted and fixed in a center hole of the ring-shaped bone grafting substitute 1; in step (c), a surgical site is covered with a membrane 3; in step (d), a gum is sutured to complete a treatment; and in step (e), after alveolar bone regeneration is completed, an implant is inserted into a screw portion, thereby completing the treatment.

Accordingly, when a bone implantation surgery is performed by using a ring-shaped bone grafting substitute, the implantation of a bone grafting substitute and the placement of an implant screw may be simultaneously performed, and thus the secondary surgical operation for the placement of an implant screw is unnecessary, thereby remarkably shortening an implant treatment period.

In this state, the thickness T of the ring-shaped bone grafting substitute 1 may be 1.5 mm to 5 mm. When the thickness is less than 1.5 mm, a ring shape may not be maintained. As a bone having an appropriate thickness is not generated around an implant, an implant may not be placed.

Furthermore, when the thickness is 5 mm or more, the size of a grafting substitute is excessively large so that inconvenience may occur during use.

Accordingly, the thickness T of a ring shape of the ring-shaped bone grafting substitute 1 is molded according to the shape and depth of an extraction socket. According to the present embodiment, the thickness T of the ring shape may be 2 mm-4 mm.

The diameter R of the center hole of the ring-shaped bone grafting substitute 1 may be 3 mm to 8 mm. When the diameter R is less than 3 mm, an implant screw may not be inserted, and when the diameter R is 8 mm or more, the strength of the ring-shaped bone grafting substitute 1 may not be maintained so that the implant screw may not be fixed.

Accordingly, the diameter R of the center hole of the ring-shaped bone grafting substitute 1 may be adjusted by using a dental cutting tool according to the thickness of an implant screw in use. According to the present embodiment, the diameter R of the center hole may be 3 mm-8 mm.

The height of the ring-shaped bone grafting substitute 1 may be adjusted according to the shape and depth of an extraction socket. According to the present embodiment, the height of the ring-shaped bone grafting substitute 1 may be 4 mm-10 mm.

Figure 3:
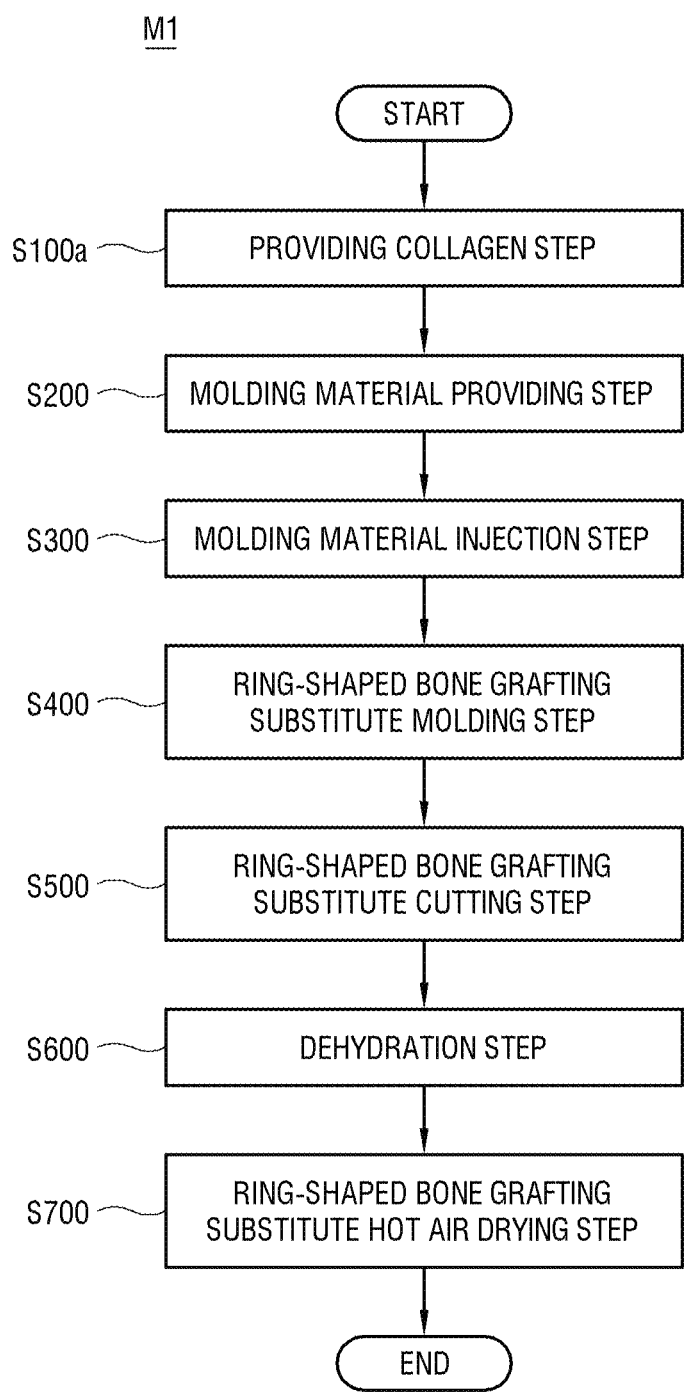
FIG. 3 is a flowchart sequentially showing a method for manufacturing a ring-shaped bone grafting substitute according to a first embodiment of the present inventive concept.

FIG. 3 is a flowchart sequentially showing a method for manufacturing a ring-shaped bone grafting substitute according to a first embodiment of the present inventive concept.

Figure 4:
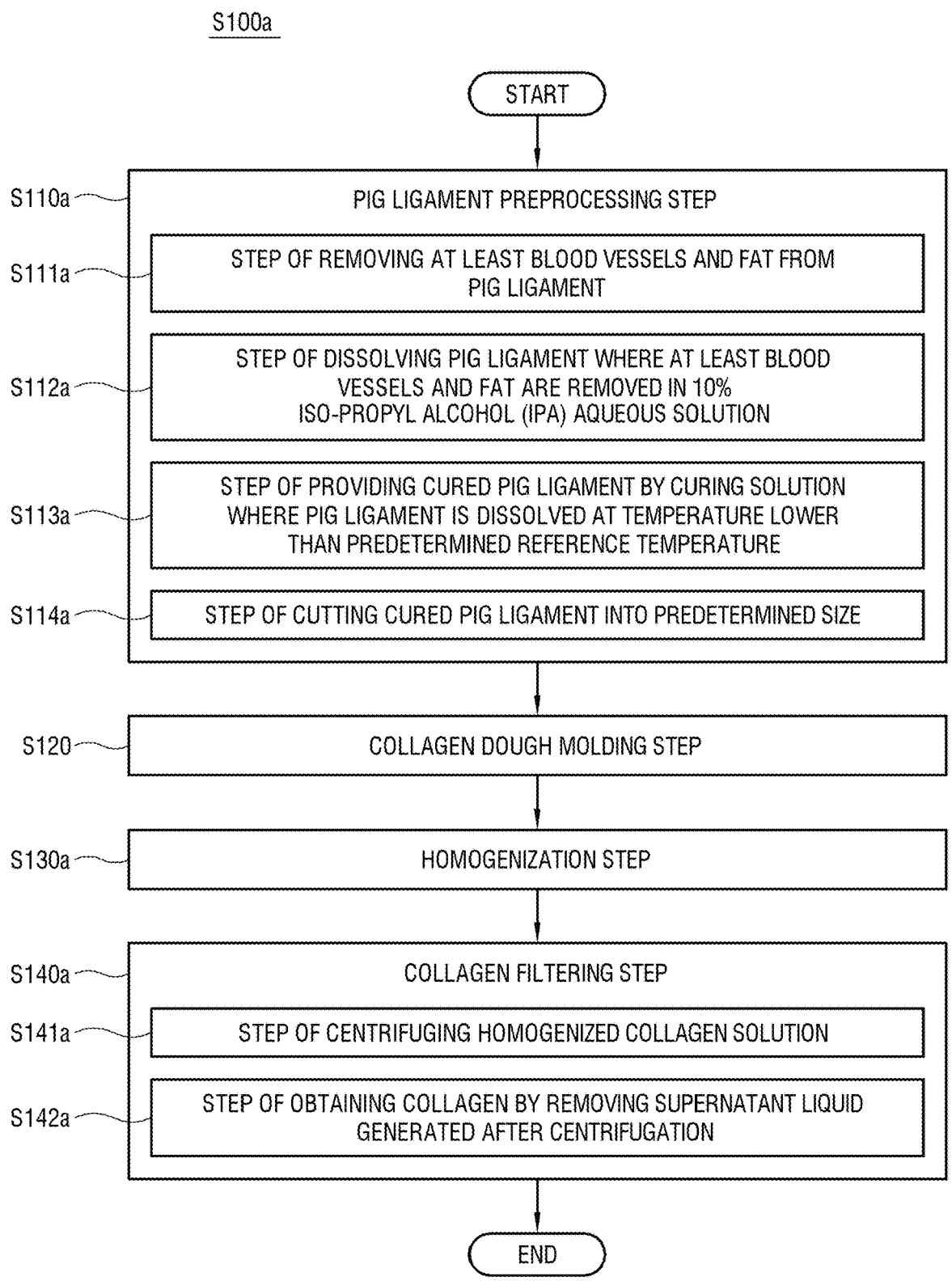
FIG. 4 is a flowchart sequentially showing a collagen providing step of providing a collagen from porcine ligament according to a first embodiment of the present inventive concept.

FIG. 4 is a flowchart sequentially showing a collagen providing step of providing a collagen from porcine ligament according to a first embodiment of the present inventive concept.

Figure 5:
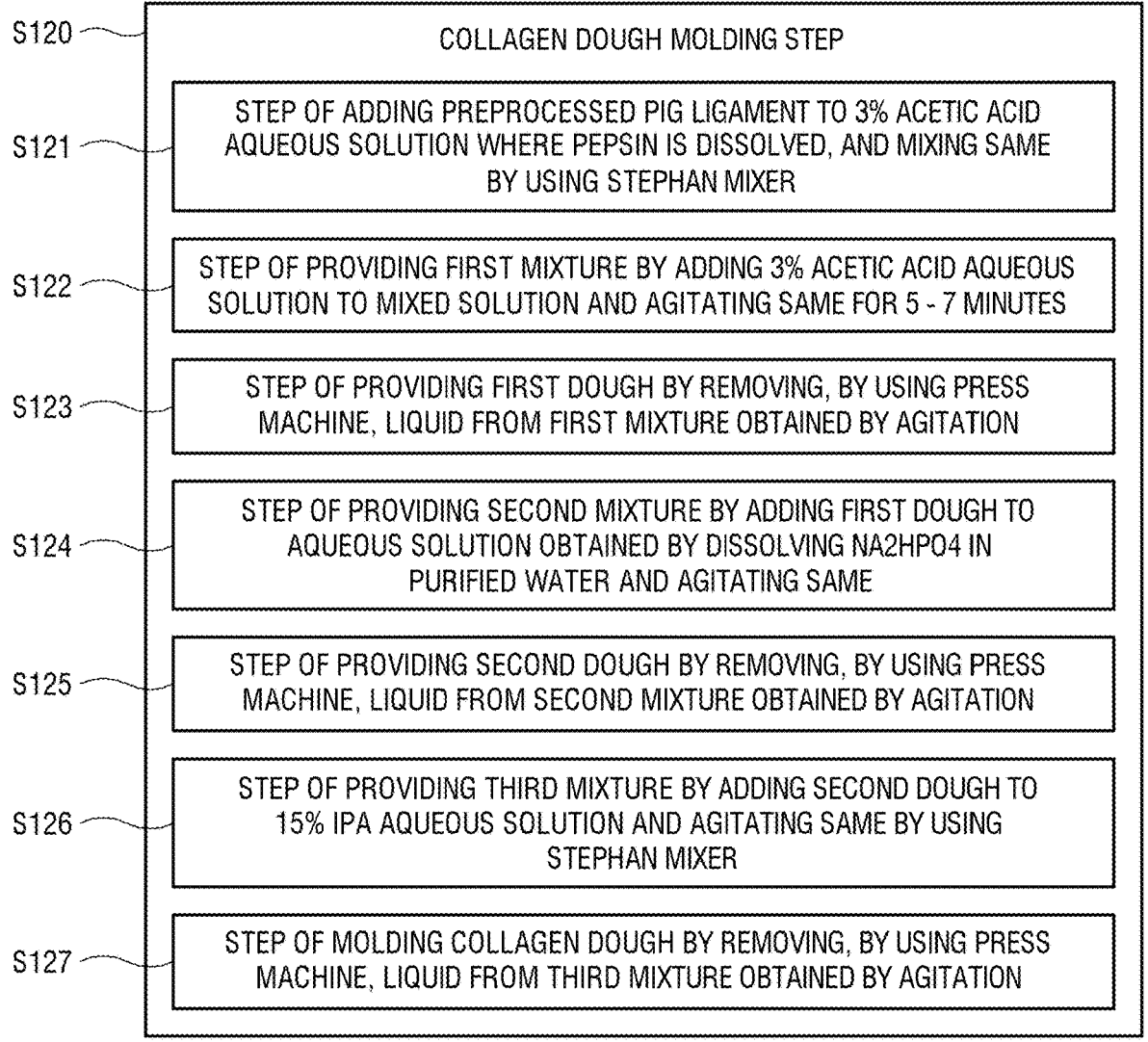
FIG. 5 is a flowchart sequentially showing a collagen dough molding step of FIG. 4.

FIG. 5 is a flowchart sequentially showing a collagen dough molding step of FIG. 4.

As illustrated in the drawings, a method M1 for manufacturing a ring-shaped bone grafting substitute according to a first embodiment of the present inventive concept may include a collagen providing step S100a, a molding material providing step S200, a molding material injection step S300, a ring-shaped bone grafting substitute molding step S400, a ring-shaped bone grafting substitute cutting step S500, a dehydration step S600, and a ring-shaped bone grafting substitute hot air drying step S700.

First, in the collagen providing step S100a, collagen to be mixed as a molding material with a bone material that is described below is provided.

The collagen is one of biodegradable polymers such as collagen, fibrinogen, chitosan, gelatin, cellulose, hyaluronic acid, dextran, and the like, crosslinked collagen, crosslinked fibrinogen, crosslinked chitosan, crosslinked gelatin, crosslinked cellulose, crosslinked hyaluronic acid, crosslinked dextran, which are crosslinked to have a crosslink structure, polycaprolactone, polylactic acid, polyglycolic acid, a copolymer of lactic acid and glycolic acid, and the like may be used therefor.

In the embodiments of the present inventive concept, a case of using collagen is mainly described. However, the disclosure is not limited thereto, and in addition to collagen, the above-exampled other biodegradable polymers may be used.

Collagen is a main component of connective tissue, as a structural protein that composes tissues and organs of the human body, and refers to an animal fibrous protein composed of about 18 amino acids such as glycine, proline, and the like. For a human, the collagen is a special structure protein that accounts for the most 35% of 5,000 types of proteins that make up the human body.

In particular, the collagen is present in the skin, bones, and tendons, and has a shape in which various amino acids are combined in the form of a polypeptide and twisted in three strands, and its molecular weight is very large, about 300,000.

There are various types of collagen according to the kind, portion, and type of animals, and the respective collagens have not only different characteristics, but also have different biomolecules or ingredients of composed protein, and the like. Accordingly, collagen that is necessarily suitable for a human body may be used.

Porcine derived collagen may be used as such collagen.

Porcine derived collagen refers to collagen extracted from tissue such as porcine skin, and the like. A pig is safe from concerns of mad cow disease, and the like, and the gene sequence of a pig is similar to that of humans, and thus the pig is being used as various substitute materials. When collagen derived particularly from a pig ligament among the porcine derived collagen is used, the collagen exhibits superior mechanical characteristics such as tensile strength, and the like The porcine derived collagen may be manufactured from the skin, tendon, tail, and the like of a pig, and particularly, may be composed of type 1, 3 collagen that has no smell and color and has a structure similar to the human body.

Furthermore, the porcine derived collagen may be safe from pathogenic infectious agents such as other animals (mad cow disease, EBS, and the like), human corpses (AIDS virus), and the like. The porcine derived collagen may have a pH value of about 7.0, a molecular weight of about 2000, and tensile strength and elongation that are superior to existing materials. Furthermore, the total protein amount of the porcine derived collagen may have a purity of 99.9%, a viscosity of 25 mps or more, and a specific gravity of 0.35-0.39.

The porcine derived collagen may include collagen from porcine ligament, collagen from porcine skin, and crosslinked collagen that is crosslinked to have a crosslink structure. According to the first embodiment of the present inventive concept, collagen from porcine ligament may be provided by using a method of providing collagen from porcine ligament. Methods of providing collagen from porcine skin and crosslinked collagen are described below in other embodiments.

First, the collagen providing step S100a of providing collagen from porcine ligament may include, as illustrated in detail in FIGS. 4 and 5, a pig ligament preprocessing step S110a, a collagen dough molding step S120, a homogenization step S130a, and a collagen filtering step S140a.

The pig ligament preprocessing step S110a, which is a step of preprocessing a pig ligament to obtain collagen from the pig ligament, may include a step S111a of removing at least blood vessels and fat from a pig ligament, a step S112a of dissolving the pig ligament where at least blood vessels and fat are removed in a 10% iso-propyl alcohol (IPA) aqueous solution, a step S113a of providing a cured pig ligament by curing a solution where the pig ligament is dissolved at a temperature lower than a predetermined reference temperature, and a step S114a of cutting the cured pig ligament into a predetermined size.

The collagen dough molding step S120, which is step of molding a preprocessed pig ligament into a collagen dough, may include a step S121 of adding the preprocessed pig ligament to a 3% acetic acid aqueous solution where pepsin is dissolved, and mixing the resultant by using a Stephan mixer, a step S122 of providing a first mixture by adding a 3% acetic acid aqueous solution to a mixed solution and agitating the resultant for 5-7 minutes, a step S123 of providing a first dough by removing, by using a press machine, liquid from the first mixture obtained by the agitation, a step S124 of providing a second mixture by adding the first dough to an aqueous solution obtained by dissolving $Na_2HPO_4$ in purified water and agitating the resultant, a step S125 of providing a second dough by removing, by using a press machine, liquid from the second mixture obtained by the agitation, a step S126 of providing a third mixture by adding the second dough to a 15% IPA aqueous solution and agitating the resultant by using a Stephan mixer, and a step S127 of molding a collagen dough by removing, by using a press machine, liquid from the third mixture obtained by the agitation.

In the homogenization step S130a, which is a step of dissolving the collagen dough in a solvent to obtain a homogenized collagen solution, a homogenized collagen solution may be obtained by agitating the collagen dough obtained from the collagen dough molding step S120 with a 10% ethanol aqueous solution by using a Stephan mixer and homogenizing the resultant by using a microfluidizer.

The collagen filtering step S140a, which is a step of filtering collagen from the homogenized collagen solution, may include a step S141a of centrifuging the homogenized collagen solution and a step S142a of obtaining collagen by removing a supernatant liquid generated after centrifugation.

The molding material providing step S200 is a step of providing a molding material by mixing a bone material in the collagen.

In this state, the bone material may be any one xenogenic bone selected from among a cattle bone, a horse bone, and a pig bone, and a synthetic bone that is artificially synthesized from a ceramic based, and the like, material may be used.

In providing a molding material by mixing the collagen and the bone material, the weight ratio of the collagen and the bone material to be mixed is related to a compressive strength of the ring-shaped bone grafting substitute.

When a biodegradable polymer including the above-described collagen is mixed with the bone material, the bone material and the biodegradable polymer may be mixed such that the weight ratio of bone material/biodegradable polymer is 60/40 to 95/5, and when the biodegradable polymer is collagen, the bone material and the collagen may be mixed such that the weight ratio of bone material/collagen is 80/20 to 95/5.

Table 1 shows a compressive strength of a bone grafting substitute according to the weight ratio of a bone material and collagen, which is experimentally obtained. As shown in the table, the compressive strength is the strongest when the weight ratio of bone material/collagen is 90/10.

TABLE 1

| WEIGHT RATIO OF BONE MATERIAL/COLLAGEN | COMPRESSIVE STRENGTH |
| --- | --- |
| 95/5 | 5 MPa |
| 90/10 | 40 MPa |
| 85/15 | 25 MPa |
| 80/20 | 15 MPa |

Accordingly, according to the present inventive concept, as a bone material and collagen are mixed by adjusting the weight ratio of a bone material and collagen to mold a ring-shaped bone grafting substitute, a ring-shaped bone grafting substitute having a strength enough to firmly fix an implant screw may be manufactured.

In this state, the collagen having passed the collagen filtering step S140a is a precipitate obtained by using a centrifugal method and is in a solid state, and the collagen is added to a 10% IPA aqueous solution, agitated by using a homogenizer, and then mixed with a bone material, thereby providing a molding material.

The molding material injection step S300 is a step of injecting the molding material into a ring-shaped mold having a ring shape to form a hole at a center thereof.

The ring-shaped bone grafting substitute molding step S400 is a step of molding a ring-shaped bone grafting substitute having a ring shape by freeze-drying the molding material injected into the ring-shaped mold at a temperature lower than a predetermined reference temperature freeze-drying.

The ring-shaped bone grafting substitute cutting step S500 is a step of cutting the ring-shaped bone grafting substitute 1 in a unit size.

When the ring-shaped mold is molded long in a height H direction of the ring-shaped bone grafting substitute 1 by changing the shape of the ring-shaped mold, a plurality of the ring-shaped bone grafting substitutes 1 may be molded by cutting the ring-shape mold in a unit size of a desired height H, and a plurality of the ring-shaped bone grafting substitutes 1, each having a different height H, may be molded.

The dehydration step S600 is a step of removing moisture included in the ring-shaped bone grafting substitute 1. In this state, by performing dehydration using 90% ethanol, any moisture remaining in the ring-shaped bone grafting substitute molding step S400 by freeze-drying may be removed.

The ring-shaped bone grafting substitute hot air drying step S700 is a step of drying, by using hot air, the ring-shaped bone grafting substitute that has been completely molded. In the present embodiment, the step S700 is performed at 70° C. for about 18 hours, but the disclosure is not limited thereto and the temperature and the time may vary according to the drying conditions.

In the following description, a process of manufacturing a ring-shaped bone grafting substitute by a method for manufacturing a ring-shaped bone grafting substitute according to a first embodiment of the present inventive concept, the method including the above-described steps, is described.

When a pig ligament of 1 kg is described as a standard, first, blood vessels, fat, and the like are removed through trimming, and the pig ligament is dipped in a 65% IPA aqueous solution of 3.45 kg for 5 minutes, washed with purified water of 3.35 kg, and cured at −80° C. The cured ligament is cut by a slicer so that preprocessing of the pig ligament is completed.

Next, a 3% acetic acid aqueous solution of 3 kg, where pepsin of 2 g is dissolved, and the cut ligament are put into the Stephan mixer and agitated for 6 minutes, a 3% acetic acid aqueous solution of 3,500 kg is put therein and agitated for 6 minutes, and the mixture is pressed by a press machine so that liquid is removed therefrom.

The obtained dough is put into the Stephan mixer with an aqueous solution obtained by dissolving $Na_2HPO_4$ of 53.6 g in purified water of 3.35 kg, agitated for 6 minutes, pressed by the press machine to remove liquid, put into the Stephan mixer with a 15% IPA aqueous solution of 3.5 kg, agitated for 6 minutes, put into the Stephan mixer by removing liquid by using the press machine, agitated for 6 minutes by adding a 15% IPA aqueous solution of 3.5 kg, and pressed by using the press machine to remove liquid, thereby being molded into collagen dough.

Next, the collagen dough is put into the Stephan mixer with a 10% ethanol aqueous solution of 5.5 kg, agitated for 6 minutes, and homogenized through a microfluidizer.

Next, a 10% IPA aqueous solution of 3.5 kg is added to the collagen obtained by removing supernatant liquid after centrifugation, the mixture is agitated by the homogenizer, and a bone material of 130 g is mixed with the mixture, thereby providing a molding material.

Next, the molding material is pour into a ring-shaped mold and then freeze-dried so that the bone grafting substitute may be molded in a ring shape.

Next, a freeze-dried ring-shaped bone grafting substitute is cut according to a desired height H, dehydrated with 90% ethanol, dried with hot air at 70° C. for 18 hours, and thus the process of manufacturing a ring-shaped bone grafting substitute is completed.

As such, according to the present embodiment, as a ring-shaped bone grafting substitute having a ring shape is molded, the implantation of a bone grafting substitute and the placement of an implant may be simultaneously performed, and thus the secondary surgical operation for implant placement is unnecessary so that an implant treatment period may be remarkably reduced.

Furthermore, as a ring-shaped bone grafting substitute is molded by mixing collagen and a bone material, a ring-shaped bone grafting substitute having a strength enough to firmly fix an implant screw may be manufactured.

Figure 6:
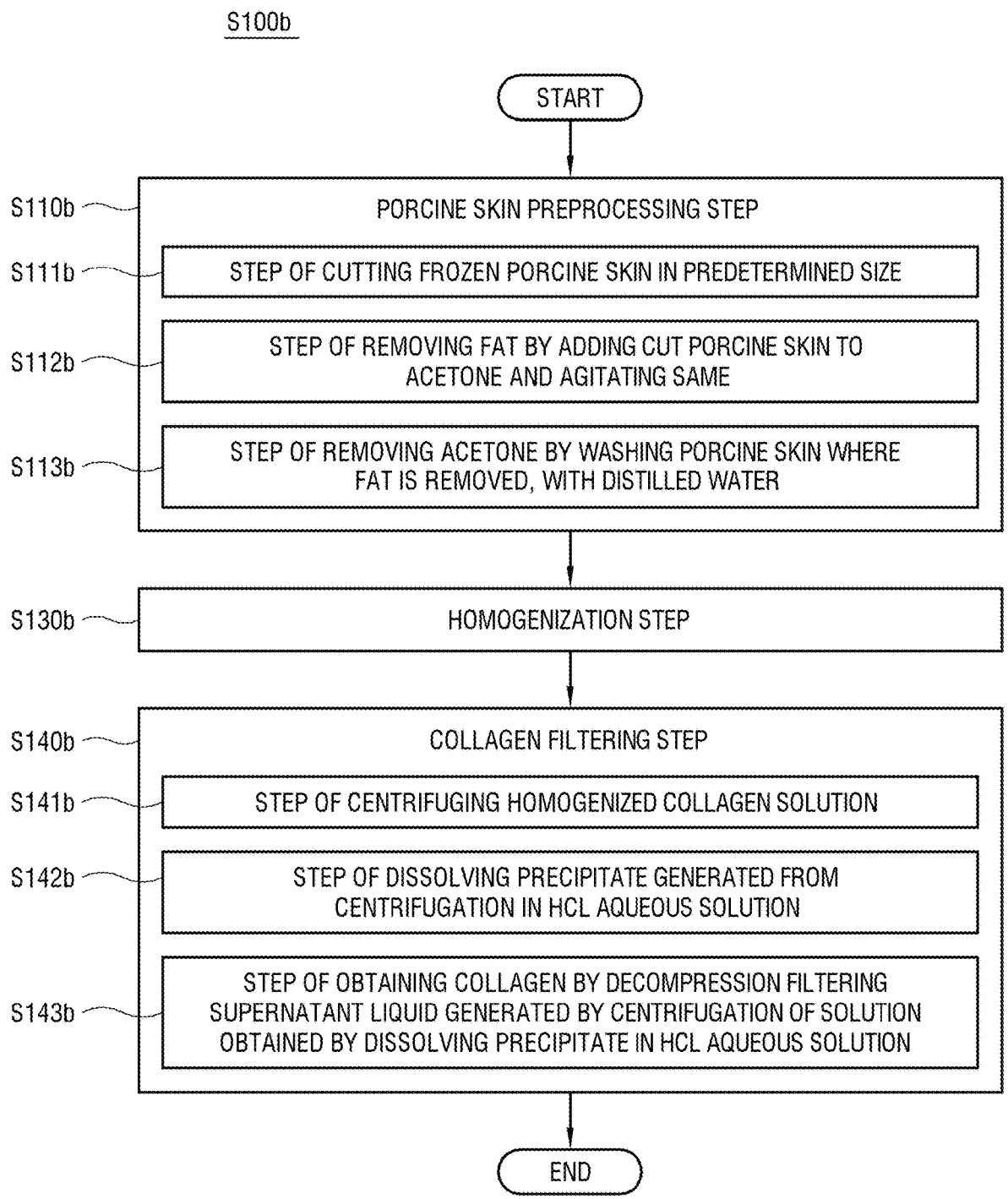
FIG. 6 is a flowchart sequentially showing a collagen providing step of providing collagen from porcine skin a second embodiment according to the present inventive concept.

FIG. 6 is a flowchart sequentially showing a collagen providing step of providing collagen from porcine skin a second embodiment according to the present inventive concept.

According to a method M2 for manufacturing a ring-shaped bone grafting substitute according to a second embodiment of the present inventive concept, when compared with the first embodiment, there is a difference in a collagen providing step S100b in that collagen from porcine skin is provided instead of collagen from porcine ligament. As there is no difference in the other steps of manufacturing a ring-shaped bone grafting substitute, the collagen providing step S100b is mainly described.

The collagen providing step S100b of providing collagen from porcine skin may include, as illustrated in detail in FIG. 6, a porcine skin preprocessing step S110b, a homogenization step S130b, and a collagen filtering step S140b.

The porcine skin preprocessing step S110b, which is a step of preprocessing porcine skin to obtained collagen from the porcine skin, may include a step S111b of cutting frozen porcine skin in a predetermined size, a step S112b of removing fat by adding the cut porcine skin to acetone and agitating the resultant, and a step S113b of removing acetone by washing the porcine skin where fat is removed, with distilled water.

In the present embodiment, after frozen porcine skin is thawed and cut into a square of 2 cm×2 cm, cut skin pieces are put into acetone, agitated for two hours twice to remove fat, and washed with distilled water five times to remove the acetone.

The homogenization step S130b is a step of dissolving the preprocessed porcine skin in a solvent to produce a homogenized collagen solution. In the present embodiment, the preprocessed porcine skin pieces is homogenized by being putting into a 3 mm HCl (pH 2.7) aqueous solution to be 3%.

A collagen filtering step S140b, which is a step of filtering collagen from the homogenized collagen solution, may include a step S141b of centrifuging the homogenized collagen solution, a step S142b of dissolving a precipitate generated from the centrifugation in a HCL aqueous solution, and a step S143b of obtaining collagen by decompression filtering a supernatant liquid generated by the centrifugation of the solution obtained by dissolving the precipitate in the HCL aqueous solution.

In the present embodiment, a homogenized aqueous solution is agitated at 4° C. for 1 day, and the precipitate obtained by centrifugation at 4° C., under a condition of 40,000 g, for 1 hour is put into 3 mm HCl.

Next, the solution is agitated at 4° C. for 3 days and centrifuged at 4° C., under a condition of 27,000 g, for 1 hour, and then the supernatant liquid is decompression filtered by using filter paper, thereby obtaining collagen.

Thereafter, the collagen from porcine skin obtained through the decompression filtering is mixed with a bone material, and thus a ring-shaped bone grafting substitute is manufactured in the same manner as the first embodiment.

Figure 7:
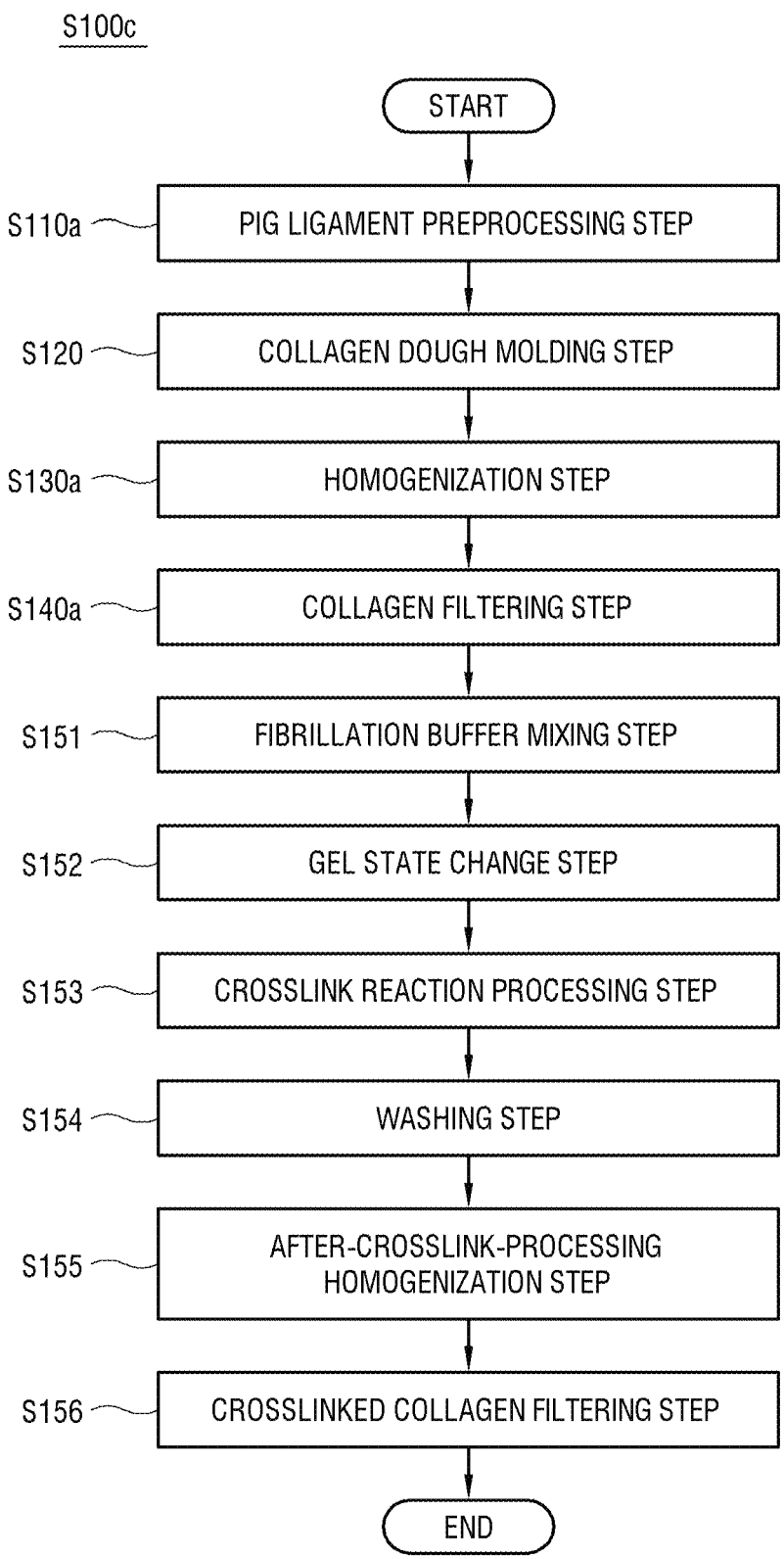
FIG. 7 is a flowchart sequentially showing a collagen providing step of providing crosslinked collagen according to a third embodiment of the present inventive concept crosslinked collagen.

FIG. 7 is a flowchart sequentially showing a collagen providing step of providing crosslinked collagen according to a third embodiment of the present inventive concept crosslinked collagen.

According to a method M3 for manufacturing a ring-shaped bone grafting substitute according to a third embodiment of the present inventive concept, the present embodiment is different from the first and second embodiments in that crosslinked collagen is provided in a collagen providing step S100c. As the other steps for manufacturing a ring-shaped bone grafting substitute are the same, the collagen providing step S100c is mainly described.

When crosslinked collagen having a crosslinked structure is in use, a ring-shaped bone grafting substitute having superior mechanical characteristics such as tensile strength, and the like may be obtained.

As illustrated in detail in FIG. 7, after the collagen providing step S100a of the first embodiment of the present inventive concept, the collagen providing step S100c of providing crosslinked collagen may further include a fibrillation buffer mixing step S151, a gel state change step S152, a crosslink reaction processing step S153, a washing step S154, an after-crosslink-processing homogenization step S155, and a crosslinked collagen filtering step S156.

However, the disclosure is not limited thereto, and the fibrillation buffer mixing step S151, the gel state change step S152, the crosslink reaction processing step S153, the washing step S154, the after-crosslink-processing homogenization step S155, and the crosslinked collagen filtering step S156 may be further provided after the collagen providing step S100b of the second embodiment of the present inventive concept.

In other words, after any one collagen selected from the collagen from porcine ligament and the collagen from porcine skin is provided, crosslinked collagen may be obtained by performing crosslink reaction processing.

First, in the fibrillation buffer mixing step S151, a mixed solution is obtained by mixing the collagen obtained from the collagen filtering step S140a or S140b with a fibrillation buffer having sodium chloride 20-30 part by weight, sodium hydroxide 1-3 part by weight, and di-sodium hydrogen phosphate dihydrate 3-5 part by weight with respect to water 100 part by weight.

Next, in the gel state change step S152, the mixed solution is mixed with y-PGA and put into a well plate to be changed to a gel state in an incubator, thereby providing a mixture in a gel state. In this state, the temperature is maintained at 4° C. or less while a vacuum state is maintained, and a 1-2 hour degassing state is maintained.

Next, in the crosslink reaction processing step S153, the gel-state mixture is mixed with a crosslinking solution to induce a crosslink reaction, thereby forming crosslinked collagen.

Next, the washing step S154, which is a step of washing the crosslinking solution mixed in the crosslink reaction processing step, may include a step S154a of providing a first mixture by tearing the crosslinked collagen into small pieces and adding the resultant to a 15% ethanol aqueous solution, a step S154b of providing a filtrate by agitating the first mixture and decompression filtering the resultant, a step S154c of providing a second mixture by tearing the filtrate into small pieces and adding the resultant to a 15% ethanol aqueous solution, and a step S154d of agitating the second mixture and decompression filtering the resultant.

The washing step S154 may be repeated twice or more according to a result of the washing step.

Next, in the after-crosslink-processing homogenization step S155, the crosslinked collagen is dissolved in a solvent to produce a homogenized crosslinked collagen solution, a 15% ethanol aqueous solution is put into a mixer, the filtrate that has been filtered by the decompression filtering of the washing step S154 is torn into small pieces and put into the mixer, agitation is performed at a fast speed for 10 minutes, and a mixture liquid is homogenized by a micro fluidizer, thereby obtaining a homogenized crosslinked collagen solution.

Next, in the crosslinked collagen filtering step S156, which is a step of filtering crosslinked collagen from the homogenized crosslinked collagen solution, the homogenized crosslinked collagen solution obtained from the after-crosslink-processing homogenization step S155 is centrifuged to remove a supernatant liquid, thereby obtaining crosslinked collagen.

Thereafter, the crosslinked collagen obtained by centrifugation is mixed with a bone material, thereby manufacturing a ring-shaped bone grafting substitute in the same method as the first and second embodiments.

As such, while this disclosure has been particularly shown and described with reference to preferred embodiments thereof, it will be understood by those of ordinary skill in the art that various changes in form and details may be made therein without departing from the spirit and scope of the inventive concept as defined by the appended claims. The preferred embodiments should be considered in descriptive sense only and not for purposes of limitation. Therefore, the scope of the inventive concept is defined not by the detailed description of the inventive concept but by the appended claims, and all differences within the scope will be construed as being included in the inventive concept.

INDUSTRIAL APPLICABILITY

The present inventive concept may be used for a medical industry, particularly for a dental industry.

The invention claimed is:

1. A method for manufacturing a ring-shaped bone grafting substitute, the method comprising:
 a biodegradable polymer providing step of providing a biodegradable polymer;
 a molding material providing step of providing a molding material by mixing the biodegradable polymer with a bone material;
 a molding material injection step of injecting the molding material into a ring-shaped mold having a ring shape to form a hole at a center; and
 a ring-shaped bone grafting substitute molding step of molding a ring-shaped bone grafting substitute having a ring shape by freeze-drying the molding material injected into the ring-shaped mold at a temperature lower than a predetermined reference temperature,
 wherein, in the molding material providing step, the bone material and the biodegradable polymer are mixed such that a weight ratio of bone material/biodegradable polymer is 60/40 to 95/5,
 wherein the biodegradable polymer comprises collagen, the collagen comprises collagen from porcine skin, and a collagen providing step of providing the collagen comprises:

a porcine skin preprocessing step of preprocessing the porcine skin to obtain collagen from the porcine skin;

a homogenization step of dissolving the preprocessed porcine skin in a solvent to produce a homogenized collagen solution; and a collagen filtering step of filtering collagen from the homogenized collagen solution, wherein the collagen comprises crosslinked collagen that is crosslinked to have a crosslink structure, wherein the method further comprises, after the collagen filtering step:

a fibrillation buffer mixing step of providing a mixed solution obtained by mixing the collagen obtained from the collagen filtering step with a fibrillation buffer having sodium chloride 20-30 part by weight, sodium hydroxide 1-3 part by weight, and di-sodium hydrogen phosphate dihydrate 3-5 part by weight with respect to water 100 part by weight;

a gel state change step of providing a mixture in a gel state by mixing the mixed solution with gamma polyglutamic acid (γ-PGA) and putting a resultant therefrom in a well plate to be changed to a gel state in an incubator;

a crosslink reaction processing step of forming crosslinked collagen by mixing the gel state mixture with a crosslinking solution to induce a crosslink reaction;

a washing step of washing the crosslinking solution mixed in the crosslink reaction processing step;

an after-crosslink-processing homogenization step of dissolving the crosslinked collagen in a solvent to produce a homogenized crosslinked collagen solution; and a crosslinked collagen filtering step of filtering crosslinked collagen from the homogenized crosslinked collagen solution.

2. The method of claim 1, further comprising, after the ring-shaped bone grafting substitute molding step, a ring-shaped bone grafting substitute hot air drying step of drying, by using hot air, the ring-shaped bone grafting substitute that has been completely molded.

3. The method of claim 2, further comprising, before the ring-shaped bone grafting substitute hot air drying step:

a ring-shaped bone grafting substitute cutting step of cutting the ring-shaped bone grafting substitute in a unit size; and a dehydration step of removing moisture included in the ring-shaped bone grafting substitute.

4. A method for manufacturing a ring-shaped bone grafting substitute, the method comprising:

a biodegradable polymer providing step of providing a biodegradable polymer;

a molding material providing step of providing a molding material by mixing the biodegradable polymer with a bone material;

a molding material injection step of injecting the molding material into a ring-shaped mold having a ring shape to form a hole at a center; and a ring-shaped bone grafting substitute molding step of molding a ring-shaped bone grafting substitute having a ring shape by freeze-drying the molding material injected into the ring-shaped mold at a temperature lower than a predetermined reference temperature, wherein, in the molding material providing step, the bone material and the biodegradable polymer are mixed such that a weight ratio of bone material/biodegradable polymer is 60/40 to 95/5, wherein the biodegradable polymer comprises collagen, the collagen comprises collagen from porcine ligament, and the collagen providing step of providing the collagen comprises:

a pig ligament preprocessing step of preprocessing the pig ligament to obtain collagen from the pig ligament;

a collagen dough molding step of molding a preprocessed pig ligament into a collagen dough;

a homogenization step of dissolving the collagen dough in a solvent to produce a homogenized collagen solution; and a collagen filtering step of filtering collagen from the homogenized collagen solution, and wherein the collagen comprises crosslinked collagen that is crosslinked to have a crosslink structure, the method further comprising, after the collagen filtering step:

a fibrillation buffer mixing step of providing a mixed solution obtained by mixing the collagen obtained from the collagen filtering step with a fibrillation buffer having sodium chloride 20-30 part by weight, sodium hydroxide 1-3 part by weight, and di-sodium hydrogen phosphate dihydrate 3-5 part by weight with respect to water 100 part by weight;

a gel state change step of providing a mixture in a gel state by mixing the mixed solution with gamma polyglutamic acid (γ-PGA) and putting a resultant therefrom in a well plate to be changed to a gel state in an incubator;

a crosslink reaction processing step of forming crosslinked collagen by mixing the gel state mixture with a crosslinking solution to induce a crosslink reaction;

a washing step of washing the crosslinking solution mixed in the crosslink reaction processing step;

an after-crosslink-processing homogenization step of dissolving the crosslinked collagen in a solvent to produce a homogenized crosslinked collagen solution; and a crosslinked collagen filtering step of filtering crosslinked collagen from the homogenized crosslinked collagen solution.

5. The method of claim 4, wherein the pig ligament preprocessing step comprises:

a step of removing at least blood vessels and fat from the pig ligament;

a step of dissolving the pig ligament where at least blood vessels and fat are removed in a 10% iso-propyl alcohol (IPA) aqueous solution;

a step of providing a cured pig ligament by curing a solution where the pig ligament is dissolved at a temperature lower than a predetermined reference temperature; and a step of cutting the cured pig ligament in a predetermined size.

6. The method of claim 4, wherein the collagen dough molding step comprises:

a step of adding the preprocessed pig ligament to a 3% acetic acid aqueous solution where pepsin is dissolved, and mixing the resultant by using a Stephan mixer;

a step of providing a first mixture by adding a 3% acetic acid aqueous solution to a mixed solution and agitating the resultant for 5-7 minutes;

a step of providing a first dough by removing, by using a press machine, liquid from the first mixture obtained by the agitation;

a step of providing a second mixture by adding the first dough to an aqueous solution obtained by dissolving Na2HPO4 in purified water and agitating the resultant;

a step of providing a second dough by removing, by using a press machine, liquid from the second mixture obtained by the agitation;

a step of providing a third mixture by adding the second dough to a 15% iso-propyl alcohol (IPA) aqueous solution and agitating the resultant by using a Stephan mixer; and a step of molding a collagen dough by removing, by using a press machine, liquid from the third mixture obtained by the agitation.

7. The method of claim 4, wherein the collagen filtering step comprises:

a step of centrifuging the homogenized collagen solution; and a step of obtaining collagen by removing supernatant liquid generated after the centrifugation.

8. The method of claim 1, wherein the porcine skin preprocessing step comprises:

a step of cutting frozen porcine skin in a predetermined size;

a step of removing fat by adding cut porcine skin to acetone and agitating a resultant therefrom; and a step of removing acetone by washing porcine skin where fat is removed, with distilled water.

9. The method of claim 1, wherein the collagen filtering step comprises:

a step of centrifuging the homogenized collagen solution;

a step of dissolving a precipitate generated from the centrifugation in a HCL aqueous solution; and a step of obtaining collagen by decompression filtering a supernatant liquid generated by centrifuging a solution obtained by dissolving the precipitate in the HCL aqueous solution.

10. The method of claim 1, wherein the washing step comprises:

a step of providing a first mixture by tearing the cross-linked collagen into small pieces and adding the resultant to a 15% ethanol aqueous solution;

a step of providing a filtrate by agitating the first mixture and decompression filtering the resultant;

a step of providing a second mixture by tearing the filtrate into small pieces and adding the resultant to a 15% ethanol aqueous solution; and a step of agitating the second mixture and decompression filtering the resultant.

11. The method of claim 1, wherein the bone material comprises any one xenogenic bone selected from among a cattle bone, a horse bone, and a pig bone.

12. The method of claim 1, wherein the bone material comprises a synthetic bone that is artificially synthetized.

13. The method of claim 1, wherein the biodegradable polymer comprises collagen, and the bone material and the collagen are mixed such that a weight ratio of bone material/collagen is 80/20 to 95/5.

14. The method of claim 1, wherein, in the ring-shaped bone grafting substitute, the ring shape has a thickness of 2 mm-4 mm.

15. The method of claim 14, wherein, in the ring-shaped bone grafting substitute, the hole at the center has a diameter of 3 mm-8 mm and a height of 4 mm-10 mm.

* * * * *